United States Patent [19]
Janssens

[11] Patent Number: 6,027,458
[45] Date of Patent: Feb. 22, 2000

[54] DEVICE FOR TAKING A TISSUE SAMPLE

[76] Inventor: Jacques Phillibert Janssens, Klein Hukststraat 5, 3500 Hasselt, Belgium

[21] Appl. No.: 09/091,403
[22] PCT Filed: Dec. 23, 1996
[86] PCT No.: PCT/BE96/00136
 § 371 Date: Jun. 22, 1998
 § 102(e) Date: Jun. 22, 1998
[87] PCT Pub. No.: WO97/24070
 PCT Pub. Date: Jul. 10, 1997
[51] Int. Cl.[7] .................................................. A61B 10/00
[52] U.S. Cl. ............................................ 600/567; 600/568
[58] Field of Search ................................... 600/567, 564, 600/565, 566, 568; 128/754, 752

[56] References Cited

U.S. PATENT DOCUMENTS

| | | | |
|---|---|---|---|
| 2,710,000 | 6/1955 | Cromer et al. | 600/567 |
| 4,306,570 | 12/1981 | Matthews | 128/754 |
| 4,461,305 | 7/1984 | Cibley | 128/754 |
| 4,919,146 | 4/1990 | Rhinehart et al. | 128/752 |
| 5,133,360 | 7/1992 | Spears | 128/754 |
| 5,375,608 | 12/1994 | Tiefenbrun et al. | 128/754 |
| 5,394,887 | 3/1995 | Haaga | 128/754 |
| 5,449,001 | 9/1995 | Terwilliger | 128/754 |
| 5,526,822 | 6/1996 | Burbank et al. | 128/754 |

*Primary Examiner*—Max Hindenburg
*Assistant Examiner*—Brian Szmal
*Attorney, Agent, or Firm*—Bacon & Thomas, PLLC

[57] ABSTRACT

Device for taking a tissue sample, characterized in that it consists of the combination of a longitudinal receiving element (1), a knife (2) which can rotate around it and which can moreover be axially moved, and a driving device (10) which provides for at least the rotating movement of the knife (2), whereby this receiving element (1) has such a section that, between said receiving element (1) and the knife (2) applied over it, is formed at least one receiving space (3) in which tissue (15) can penetrate and can be collected, whereby the knife (2) works in conjunction with the outside of the longitudinal element (1) to cut off tissue collected in the receiving space (3) as the knife (2) is applied in a rotating manner over the longitudinal element (1).

20 Claims, 5 Drawing Sheets

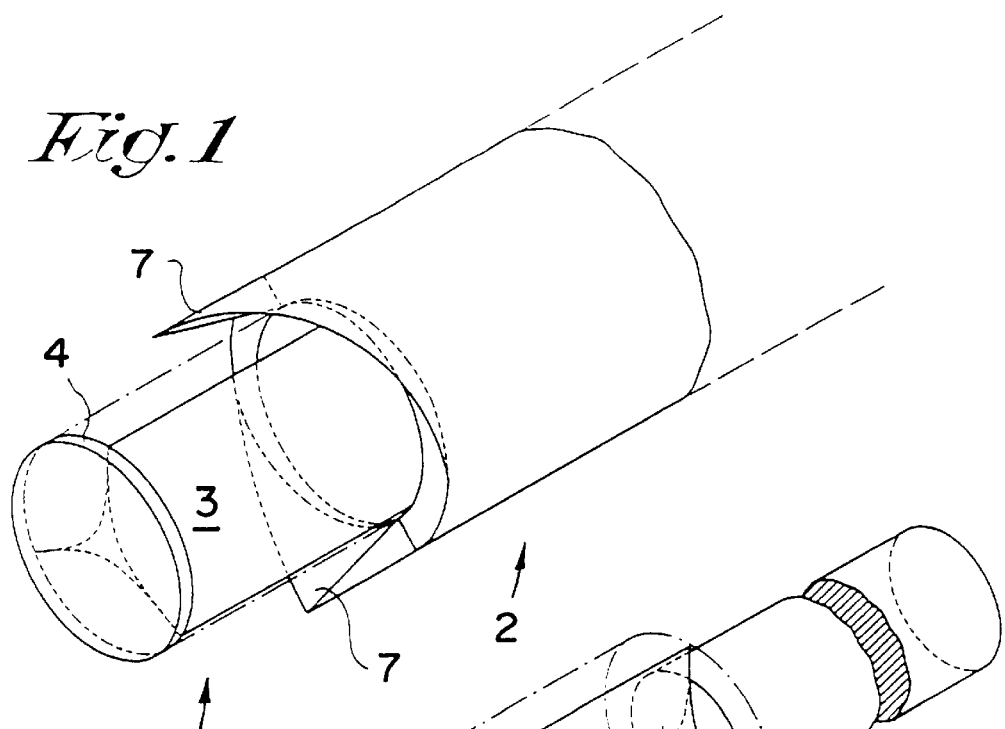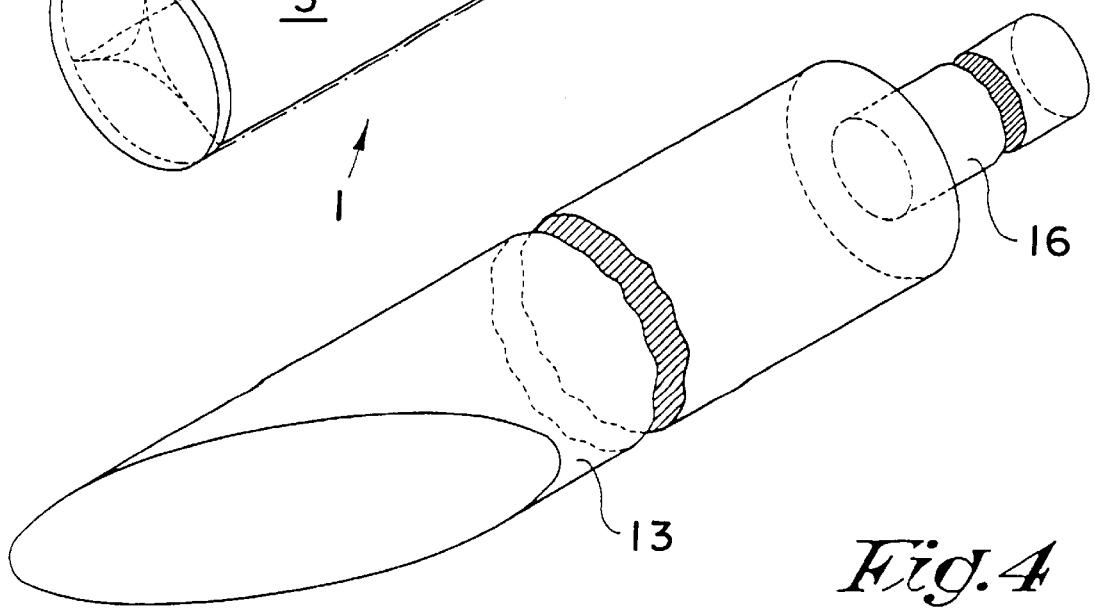

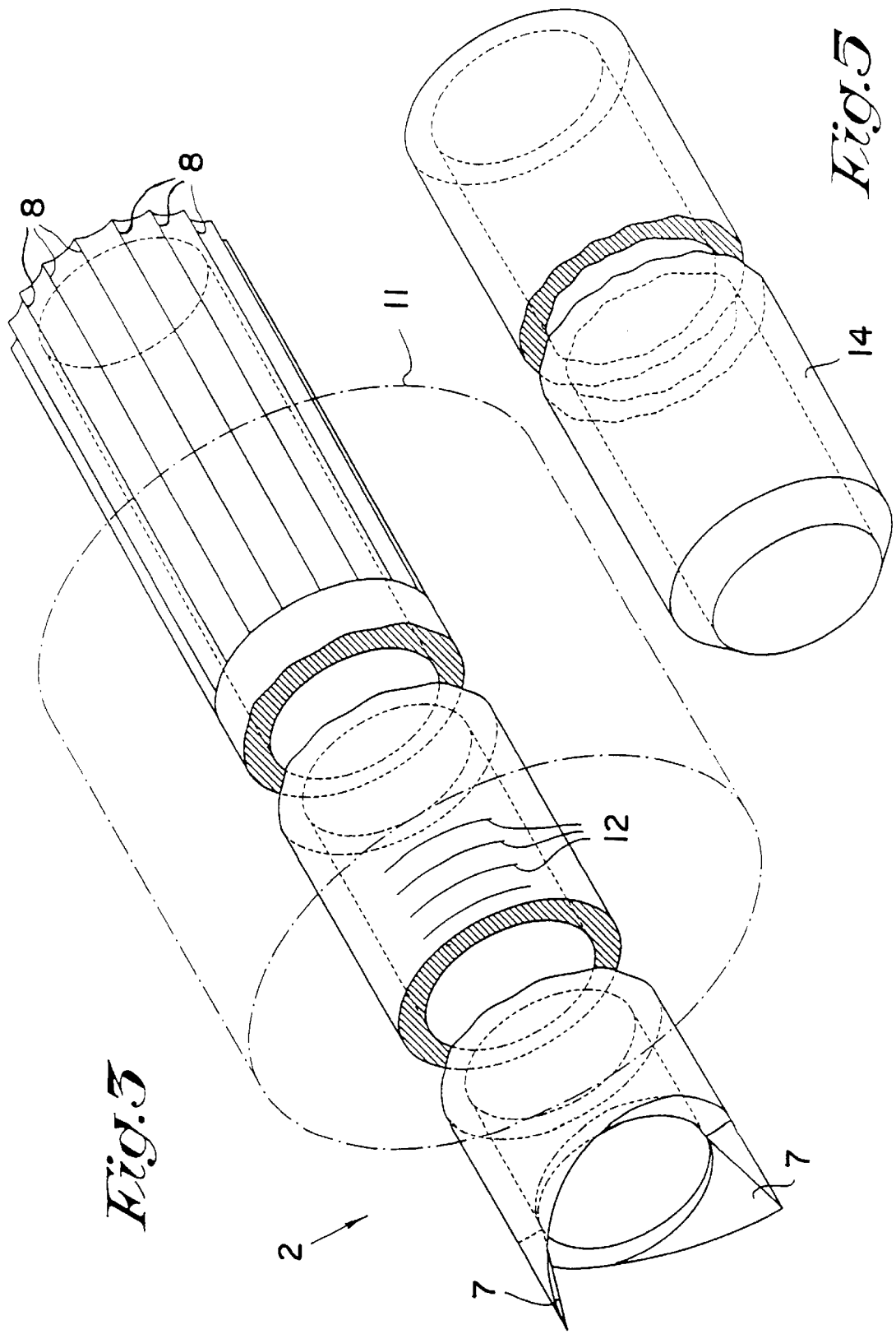

DEVICE FOR TAKING A TISSUE SAMPLE

BACKGROUND OF THE INVENTION

The present invention concerns a device for taking a tissue sample from a living human being or mammal, in other words a biopsy device.

In particular, the invention concerns a device for taking a sample from a tough tissue.

Such devices are already known, but they are often disadvantageous in that they damage the removed and/or surrounding tissue or in that they are not suitable for tough tissues such as the female breast tissue.

Another disadvantage of the known devices is that, due to their shape and dimensions, they take up too much space in order to be used in combination with an ultra-sound scan or radiological research.

Devices for taking a tissue sample are known among others from DE 2.622.850, U.S. Pat. No. 5,394,887, U.S. Pat. No. 5,499,001 and U.S. Pat. No. 4,461,305.

According to DE 2.622.850, use is made of a body which is provided with a recess, whereby a sleeve can be slid over this body with which the recess can be closed off. While the tissue sample is being taken, the sleeve remains shifted towards the back, and the entire device is moved in a rotating, sticking manner, so that a sawing effect is created, as a result of which tissue is separated in the recess 3. The above-mentioned sleeve does not provide for a cutting effect and exclusively serves to cut off the tissue which is present in the recess 3 from the environment, after the device has been removed. It is clear that the surrounding tissue as well as the tissue sample are severely damaged due to the above-mentioned movements.

A device is known from U.S. Pat. No. 5,394,887 with a rotating stiletto or receiving element and a sliding knife provided axially opposed to it which cannot carry out a rotation, however. The tissue sample is taken by providing the receiving element in the tissue, by rotating it and subsequently sliding the knife over the receiving element. The cutting speed obtained with this sliding movement is very limited, however, so that a nice cut is excluded. Moreover, the tissue is damaged due to the rotation of the stiletto.

A similar device is known from U.S. Pat. No. 5,449,001, with similar disadvantages.

A device is known from U.S. Pat. No. 4,461,305 whereby the tissue sample is separated by carrying out a scraping movement, which of course causes the surrounding tissue to be damaged. Moreover, it is only possible to take a superficial tissue sample with this device.

SUMMARY OF THE INVENTION

The present invention aims a device with which it is possible to take undamaged tissue samples with a minimum of injuries to the part of the body to be examined and the attendant pains, and which can be easily used in combination with medical imaging and subsequent laboratory research.

To this aim, the present invention consists of a biopsy device, comprising a longitudinal receiving element which at its circumference is provided with at least one lengthwise directed tissue receiving space, a knife consisting of a hollow needle which is provided at one end with a cutting edge, whereby this knife works in conjunction with the outside of the longitudinal element to cut off tissue collected in the receiving space, characterised in that the knife is rotatable around and axially movable along said receiving element, and is designed for a helicoidal rotating cutting action, whereas the receiving element is in a fixed position, and in that the device is provided with a driving device to drive the knife at least in a rotating manner over the receiving element.

The receiving element can form several receiving spaces and can have a star-shaped section with sides which are excavated for example towards the inside.

The edges of these receiving spaces are preferably sharp.

The longitudinal receiving element may have a point, but this is not necessary if for example auxiliary elements of the device are used which consist of a location needle and a stabilisation needle fitting around it which, after the location needle has been removed, forms a cavity to insert the receiving element.

BRIEF DESCRIPTION OF THE DRAWINGS

In order to better explain the characteristics of the invention, the following preferred embodiment of a device according to the invention is described as an example only without being limitative in any way, with reference to the accompanying drawings, in which:

FIG. 1 schematically shows a perspective view of a device according to the invention;

FIG. 2 shows a perspective view of the longitudinal receiving element of the device in FIG. 1 to a greater detail;

FIG. 3 shows a perspective view of the knife of the device of FIG. 1 to a greater detail;

FIGS. 4 and 5 show a perspective view of two auxiliary elements of the device according to the invention;

FIGS. 14 to 16 concern a variant of the device according to the invention, in which FIG. 16 is a section according to line XVI—XVI in FIG. 15;

DETAILED DESCRIPTION OF THE PREFERRED EMBODIMENTS

Figure 6:
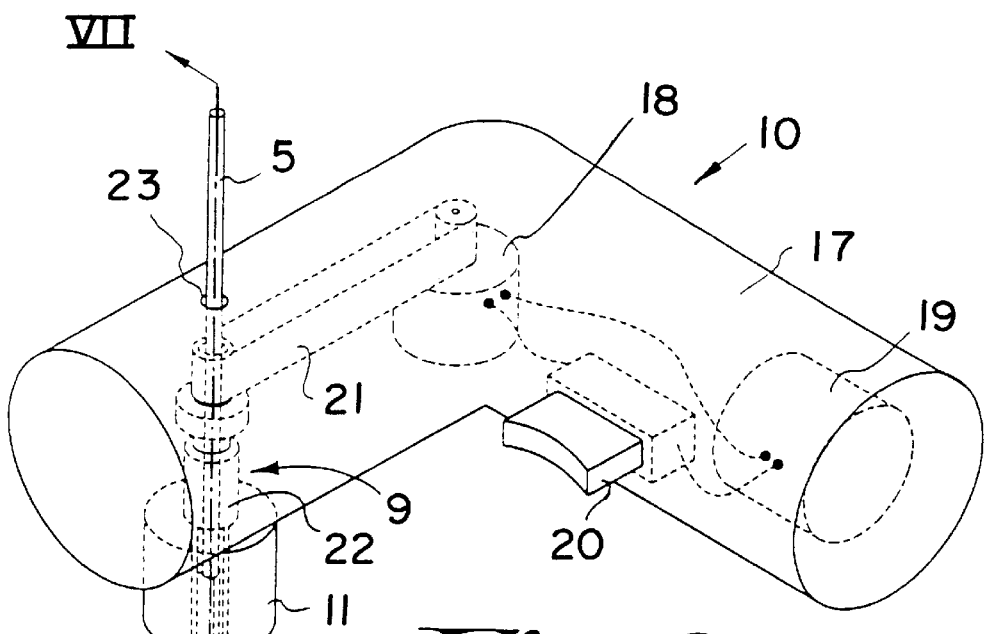
FIG. 6 shows a view of the device according to the invention while a tissue sample is being taken.
Figure 7:
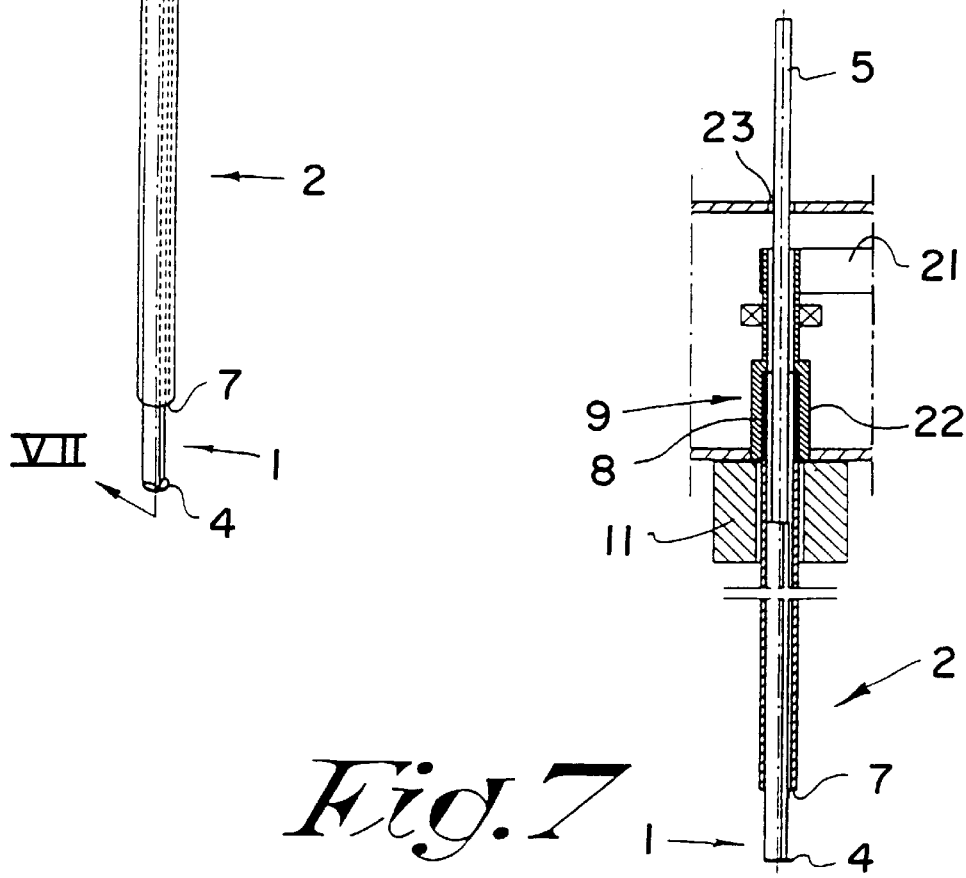
FIG. 7 shows a section according to line VII—VII in FIG. 6.

The device for taking a tissue sample according to FIG. 1 mainly contains a longitudinal receiving element 1 and a rotatable and moreover axially moveable knife 2 fitting around it.

As is represented in detail in FIG. 2, the longitudinal receiving element 1 has a cross section which is such that at least one longitudinal receiving space 3 is formed between this receiving element 1 and a theoretically enveloping imaginary circumference peripherally enclosing the element (1) and which coincides with the path of the rotatable knife 2 which is shifted over the receiving element 1 and which is represented in FIG. 2 as a chain line.

This section is preferably star-shaped and triangular in the example shown, with the sides excavated towards the inside, so that the receiving element 1 is provided with three lengthwise receiving spaces 3 separated by radial portions of the element.

The longitudinal edges of the receiving spaces 3 are quite sharp.

The receiving element 1 has a variable length up to about 10 cm with an outside diameter of for example 1.4 mm. In the figures, especially in FIG. 6, it is represented proportionally thicker than in reality for clarity's sake.

To one end of the receiving element 1 is connected a little foot 4 which consists of a washer or a short cylinder with the same diameter as the diameter of the above-mentioned theoretically enveloping cylinder.

At the other end of the receiving element 1 is attached an extension piece 5 in the shape of a little bar or a thick wire with a length of for example up to some 20 cm.

Near the last-mentioned end of the receiving element 1 is provided a calibration 6.

As is represented in detail in FIG. 3, the knife 2 consists of a hollow needle which is provided at one end with one or several cutting edges 7, in the example shown with two cutting edges 7, having a height of for example two millimetre, and which is provided at the other end over a distance of about 1 cm with a relief 8, for example ribs or grooves, which are part of a quick coupling 9 with a driving device 10 which will be further described.

The cutting edges 7 are preferably helicoidal. The gradient of the cutting edge or cutting edges 7 can be selected as a function of the ratio between the speed of the movement of rotation and the speed of the axial movement.

The knife 2 is for example about 12 cm long and has an inner diameter which coincides with the outer diameter of the receiving element 1 or the diameter of the enveloping cylinder thereof, namely 1.4 mm, and an outer diameter of 1.6 mm.

On this knife 2 can be slid a ring-shaped stabilizer 11 of for example 1 cm thick for a possible manual guiding of the knife 2.

At about 1 cm of the relief 8 is provided a calibration 12 on the knife 2.

Further, the device preferably but not necessarily contains two auxiliary elements, namely a location needle 13 and a stabilisation needle 14 fitting over it, to simplify the insertion of the receiving element 1 in the tissue 15.

The location needle 13 is represented in FIG. 4 and is a closed or solid needle having the same length as the receiving element 1, including the foot 4, and having the same diameter as said receiving element 1. This location needle 13 is fixed at the end which is moved away from its point, i.e. its outmost end, to a wire 16 with a length of for example 20 cm.

The stabilisation needle 14, which is represented in FIG. 5, is a hollow needle which is as long as the location needle 13 and which has an inner diameter of 1.4 mm and an outer diameter of 1.6 mm. At one end, the edge of the stabilisation needle 14 is bevelled, so that the hollow stabilisation needle 14 is somewhat shorter on the outside than on the inside.

The receiving element 1 with the foot 4 and the extension piece 5, the knife 2, the location needle 13 and the stabilisation needle 14 are made of stainless steel. The stabilisator 11 is made of stainless steel or of synthetic material.

The above-mentioned driving device 10 preferably has a housing 17, for example in the shape of a gun, in which is mounted an electric motor 18 which is fed by means of batteries 19 and which is operated by means of a trigger 20.

Via a transmission 21, the motor 18 drives a hollow holder 22 which works in conjunction with the relief 8 so as to hold the knife 2 with this relief 8 in the holder 21, for example by means of clamping or snapping, and which is thus also part of the above-mentioned quick coupling 9.

Above the holder 22 and in the extension thereof, the housing 17 is provided with a passage 23 for the extension piece 5.

The working of the device according to the invention is very simple and as follows, with reference to the FIGS. 8 to 13.

Before proceeding to a biopsy in the breast, an ultra-sound scan or radioscopy is carried out to locate the required sample. During this ultra-sound scan or radioscopy, the location needle 13 is pricked in the tissue 15 of the breast, preferably after a local anaesthesia, up to or past the spot where the tissue sample should be taken.

Figure 8:
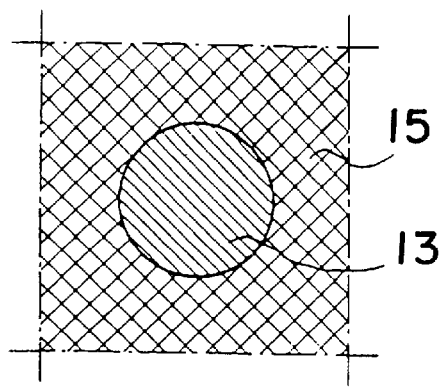
FIGS. 8 to 13 show sections of the tissue during the successive steps for taking a tissue sample.

Once the location needle 13 is positioned, as represented in FIG. 8, the stabilisation needle 14 is pushed over it with its bevelled edge forward, whereby this bevelled edge facilitates the penetration in the tissue 15.

Figure 9:
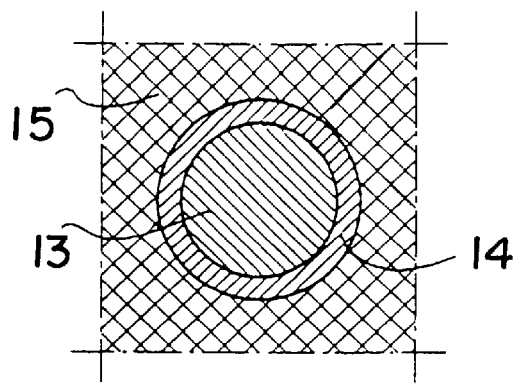
Figure 10:
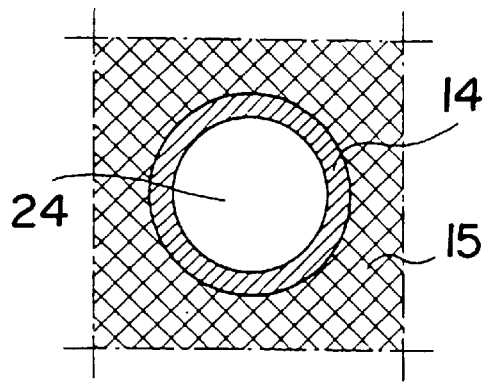

When the stabilisation needle 14 is pushed entirely over the location needle 13, as is represented in FIG. 9, the location needle 13 is withdrawn from the tissue 15 by means of the wire 16 fixed to it. Inside the stabilisation needle 14, a cylindrical cavity 24 is thus obtained as represented in FIG. 10.

Figure 11:
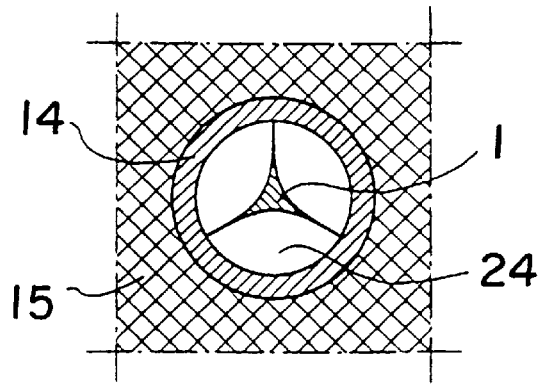

The receiving element 1 is now pushed in this cavity 24 in the stabilisation needle 14, so that it takes up the position of the location needle 13 as is represented in FIG. 11. Between the receiving element 1 and the stabilisation needle 14, the three receiving spaces 3 are formed in which the samples will be collected later on. The calibration 6 displays how far the receiving element 1 still protrudes outside the body.

The receiving element 1 is then held by means of the extension piece 5 and the stabilisation needle 14 is removed, so that only the receiving element is left over.

Figure 12:
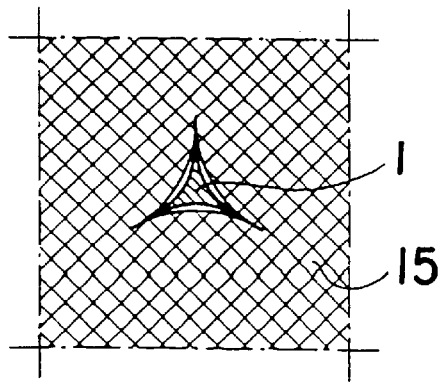
Figure 13:
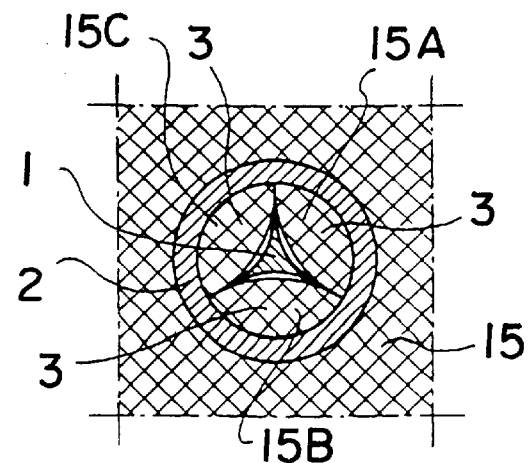

The tissue which was moved aside by the stabilisation needle 14 now sinks in the above-mentioned receiving spaces 3, formed by the specific section of the receiving element 1, as is represented in FIG. 12. Thanks to the sharp edges of the receiving element 1, the tissue which is collected in the receiving spaces 3 is separated more or less in strips.

The extension piece 5 of the receiving element 1 is put through the knife 2, the holder 22 and the passage 23 of the housing 17 of the drive mechanism 10.

The knife 2, either or not with a stabilizer 11, is then pushed over the receiving element 1 up against the patient's body, and its relief 8 is provided in the holder 22.

By operating the trigger 20 with one hand, the motor 18 is started, so that, via the transmission 21, the knife 2 is driven at high speed.

While the trigger 20 is being pressed in, the drive mechanism 10 is moved towards the body, so that the knife 2 follows a cylindrical path which coincides with the above-mentioned enveloping cylinder jacket of the receiving element 1.

When a stabilizer 11 is used, the knife 2 can be guided with the other hand during the insertion.

The knife 2 has penetrated sufficiently in the tissue 15 as soon as its cutting edges 7 reach the foot 4 of the receiving element 1. Given the dimensions of the receiving element 1 and the knife 2, this coincides with the moment when the starting point of the calibration 12 on the knife 2 is situated opposite the end of the receiving element 1, which is also the starting point of the calibration 6 on this receiving element 1

Since the distance between the above-mentioned end of the receiving element 1 and the body of the patient can be read from the calibration 6, the knife 2 has penetrated sufficiently when the same distance is read from the calibration 12 of the knife 2.

In this manner, the tissue which is situated in the receiving spaces 3 of the receiving element 1 is cut off by the knife 2, up against the foot 4.

Thanks to the presence of the foot 4, the tissue is cut off to the bottom, and the tissue strips do not need to be ripped off at their ends.

Finally, the knife 2, together with the receiving element 1 and the strips of cut-off tissue collected therein, are removed from the patient's body, and the strips of tissue can be either or not removed from the receiving spaces 3 of the receiving element 1 and immersed in a fixing bath, after which they can be taken, either or not in the receiving element 1, to a lab for anatomopathologic research or any other research whatsoever It is clear that the invention is by no means restricted to the embodiment given as an example and represented in the accompanying drawings; on the contrary, such an embodiment according to the invention can be made in all forms and dimensions while still remaining within the scope of the invention as claimed.

Thus, the section of the receiving element 1 may have another form. However, a receiving element with only two receiving spaces is usually not stable enough, whereas a receiving element with four receiving spaces usually does not allow the tissue to sink sufficiently.

A receiving element of a device according to the invention can also be carried out with a point instead of a foot, in which case the receiving element can possibly be pricked directly in the body and the auxiliary elements consisting of the location needle and the stabilisation needle may be redundant.

Figure 14:
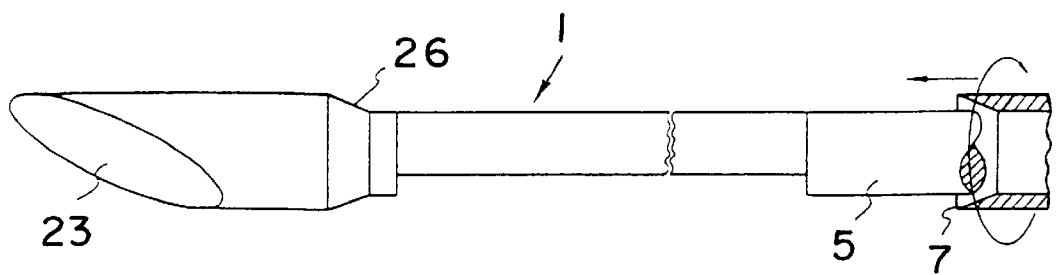
Figure 15:
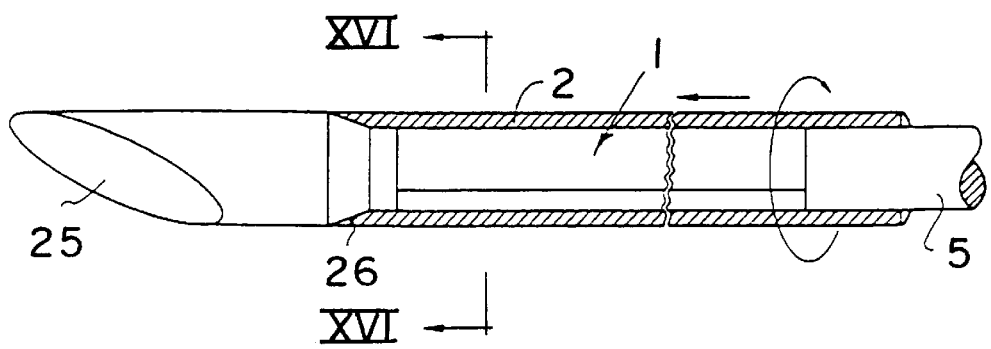
Figure 16:
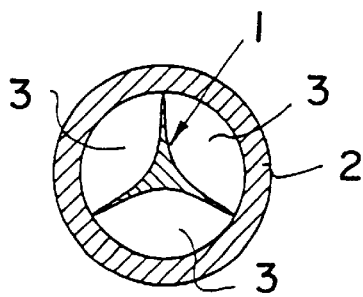

An example thereof is represented in FIGS. 14 to 16, whereby FIG. 14 represents the receiving element 1 provided with a point 25, whereas FIGS. 15 and 16 represent this receiving element 1 together with the knife 2 provided over it.

FIG. 15 shows that the cutting edge 7 of the knife 2 must not necessarily be carried out helicoidally.

The device is preferably provided with elements forming a stop which restrict the axial movement of the knife 2 in relation to the receiving element 1, so that the knife 2 cannot penetrate any deeper in the tissue than is necessary. In the embodiment of FIGS. 14 to 16, these means consist of a stop 26 provided on the receiving element 1. According to a variant, the means forming a stop can be integrated in the driving device 10.

Figure 17:
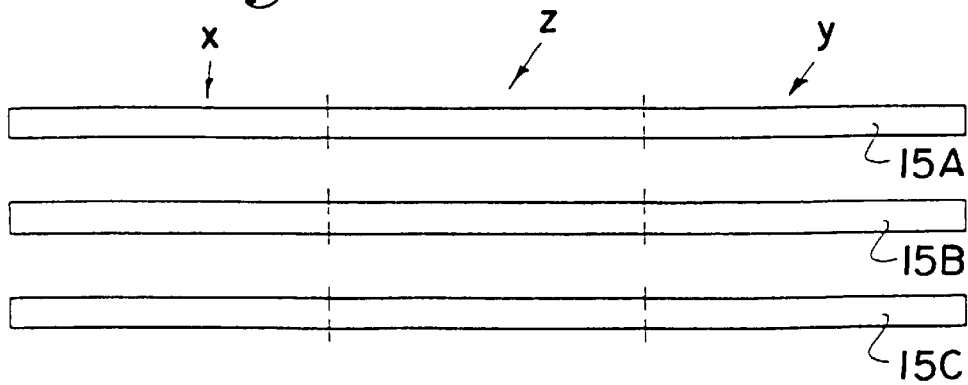
FIG. 17 shows a series of tissue samples as can be obtained according to the invention.

It should be noted that, as is the case in the embodiments represented in the figures, the receiving element 1 preferably contains at least three longitudinal receiving spaces 3 situated next to one another and separated in relation to one another. In this way can be obtained three separate, similar tissue samples 15A–15B–15C, as is schematically represented in FIG. 17, which geographically cover several areas due to the fact that they are longitudinal, by which is implied an area X which represents the deeper situated tissue, an area Y which represents the tissue situated near the surface and an area Z which represents the tissue situated in between.

In this manner, by taking a single tissue sample, several tests can be carried out on the tissue, and results for different geographical areas X-Y-Z can be obtained at the same time. The three tissue samples 15A–15B–15C make it possible to carry out for example a bacteriological, a pathological and a chemical test on the same tissue.

As described above, the driving device 10 is preferably motorized. It must not necessarily be an electric motor. By a motor can for example also be understood in this case a system which can be tightened, for example by means of a spring, and which as a result of the release provides for the rotation of the knife 2. It should be noted that the receiving element 1 is locked so that it cannot rotate, or in other words it is fixed. Consequently, this receiving element 1 is very stable.

As the knife 2 is driven in a rotating manner, and the cutting effect is not merely obtained by an axial movement, this offers the advantage that the knife 2 has the time to develop a considerable speed, so that a better cutting effect is obtained. In this manner it is possible to cut off very fine strips of tissue, so that several receiving spaces 3 can be provided for as mentioned above, without the receiving element 1 having to have a large diameter. This is not possible with the devices described in U.S. Pat. No. 5,394,887 and U.S. Pat. No. 5,449,001.

Preferably, the knife 2 is driven at a peripheral velocity of at least 10 cm per second.

The receiving element and the knife must not necessarily be provided with a calibration. The depth in the patient's body can be simply measured or estimated, which can possibly be facilitated by providing a mark on for example the knife.

Naturally, the above-mentioned dimensions are given as an illustration only.

I claim:
1. Biopsy device comprising:
    a longitudinal receiving element (1) which about an imaginary circumference peripherally enclosing the element is provided with at least one lengthwise directed tissue receiving space (3) located about the outer periphery of the receiving element (1), a knife (2) comprising a hollow needle which is provided at one end with at least one cutting edge (7), the knife (2) cooperating with the outer periphery of the receiving element (1) to cut off tissue collected in the receiving space (3), the knife (2) being rotatable around and axially movable along the length of the receiving element (1), the knife (2) configured to produce a cutting action upon helicoidal rotation in cooperation with the receiving element (1) while the receiving element (1) is maintained in a fixed position; and a driving device (10) connectable to the knife (2) to rotate the knife (2).

2. Biopsy device according to claim 1, in that the receiving element (1) has such a section that, between this receiving element wherein several receiving spaces (3) are formed between the receiving element (1) and the applied knife (2).

3. Biopsy device according to claim 1, wherein longitudinal edges of the receiving element (1) are sharp.

4. Biopsy device according to claim 1, wherein the receiving element (1) has a star-shaped section.

5. Biopsy device according to claim 3, wherein the receiving element (1) has a triangular cross-section with sides excavated toward the inside and along the length of the receiving element (1).

6. Biopsy device according to claim 1, wherein the longitudinal receiving element (1) is connected to an extension piece (5) at one end.

7. Biopsy device according to claim 4, wherein the receiving element (1) has a foot (4) at one end with an outer diameter similar in dimension to the axial extensions of the receiving element (1) enclosed by the imaginary circumference.

8. Biopsy device according to claim 1, wherein the knife (2) has at least one cutting edge (7) at one end.

9. Biopsy device according to claim 7, wherein the cutting edge or cutting edges (7) are helicoidal.

10. Biopsy device according to claim 1, further comprising auxiliary elements having a location needle (13) and a stabilization needle (14) fitting around the location needle (13) which, after the location needle (13) has been removed, forms a cavity (24) into which the receiving element (1) may be inserted.

11. Biopsy device according to claim 1, wherein the knife (2) is connectable to the driving device (10) by rapid coupling.

12. Biopsy device according to claim 1, wherein the driving device (10) is motorized.

13. Biopsy device according to claim 11, wherein the driving device is arranged to drive the knife (2) at a peripheral velocity of at least 10 cm per second.

14. Biopsy device according to claim 1, wherein the receiving element (1) is provided with a point (25).

15. Biopsy device according to claim 1, further comprising a stop (26) which is located and configured so that the stop restricts the lengthwise movement of the knife (2) after the tissue to be removed has been cut completely from surrounding tissue.

16. Biopsy device according to claim 1, wherein the receiving element (1) contains at least three longitudinal receiving spaces (3) situated circumferentially adjacent one another and separated in relation to one another by a radial portion of the receiving element (1).

17. Biopsy device according to claim 1, wherein the receiving element (1) is fixed and cannot rotate while the knife is cutting tissue.

18. Biopsy device according to claim 1, wherein the receiving element (1) includes three lengthwise directed tissue receiving spaces (3).

19. Biopsy device according to claim 1, wherein the receiving space (3) is located between the outer surface of the receiving element (1) and the inner wall of the knife (2).

20. Biopsy device comprising:

a longitudinal receiving element (1) which about an imaginary circumference peripherally enclosing the element is provided with at least two lengthwise directed tissue receiving spaces (3) located about the outer periphery of the receiving element (1), a knife (2) comprising a hollow needle which is provided at one end with at least one cutting edge (7), the knife (2) cooperating with the outer periphery of the receiving element (1) to cut off tissue collected in the receiving space (3), the knife (2) being rotatable around and axially movable along the length of the receiving element (1), the knife (2) configured to produce a cutting action upon helicoidal rotation in cooperation with the receiving element (1) while the receiving element (1) is maintained in a fixed position; and a driving device (10) connectable to the knife (2) to rotate the knife (2).

* * * * *